United States Patent [19]

Mooradian et al.

[11] Patent Number: 4,475,816

[45] Date of Patent: Oct. 9, 1984

[54] METHOD FOR DETERMINING IN SITU THE ABSORPTION COEFFICIENT OF PARTICULATE MEDIA USING PULSED LASER TECHNIQUE

[75] Inventors: Gregory C. Mooradian, Del Mar; Larry B. Stotts, Chula Vista, both of Calif.

[73] Assignee: The United States of America as represented by the Secretary of the Navy, Washington, D.C.

[21] Appl. No.: 121,937

[22] Filed: Feb. 15, 1980

[51] Int. Cl.$^3$ ............................................. G01N 21/00
[52] U.S. Cl. ..................................... 356/437; 356/338
[58] Field of Search ............... 356/337, 338, 341, 432, 356/433, 434, 436, 437, 438, 441, 442

[56] References Cited

U.S. PATENT DOCUMENTS 3,519,354 7/1970 Brown .................................. 356/436

OTHER PUBLICATIONS

Arnush, D., "Underwater Light Beam Propagation in the Small-Angle-Scattering Approximation", JOSA, vol. 62, No. 9, (Sep. 1972), pp. 1109-1111.

Bucher, E. A., "Computer Simulation of Light Pulse Propagation for Communication through Thick Clouds", *Applied Optics*, vol. 12, No. 10, (Oct. 1973), pp. 2391-2400.

*Primary Examiner*—R. A. Rosenberger
*Attorney, Agent, or Firm*—Robert F. Beers; Ervin F. Johnston; Thomas Glenn Keough

[57] ABSTRACT

A true indication of a fluid's absorption coefficient takes into effect the contributing factors of absorption and particle multiple scattering. A pulsed optical source transmits radiation through a relatively large volume of a certain particulate fluid medium. A detector or irradiance meter is gated so as to provide waveforms on a monitor which are characteristic of the absorption and multiple scattering of the medium. Using the transmittance and multiple line spread of the received signal a nearly real-time in situ analysis can be performed to provide scientists, communications specialists, etc. with the capability to anticipate operational parameters.

2 Claims, 6 Drawing Figures

ABSORPTION & SCATTERING $\frac{P_o}{P_i} = e^{-\alpha R(1+\delta)}$

SCATTERING ONLY $\frac{P_o}{P_i} = 1$

ABSORPTION ONLY $\frac{P_o}{P_i} = e^{-\alpha R}$

METHOD FOR DETERMINING IN SITU THE ABSORPTION COEFFICIENT OF PARTICULATE MEDIA USING PULSED LASER TECHNIQUE

BACKGROUND OF THE INVENTION

The development of short pulse optical communication systems or long range optical imagers for use in the oceanic transmission channel requires accurate knowledge of the effects of absorptive, particulate multiple scattering on the transfer of optical radiation. Generally speaking, this multiple scattering process inhibits optimum system performance by inducing such things as an additional beam spread, energy loss, a degradation of spatial coherence, depolarization, and a dispersion in time and frequency of the signal modulating the initial radiance distribution. Hence, a receiver is compromised by having increased design complexity with diminished performance in return for increased operational range. An in-depth study was presented by R. C. Honey and G. P. Sorenson and entitled "Optical Absorption and Turbulence-induced Narrow-angle Forward Scatter in the Sea" at the AGARD Conference No. 77 on "Electromagnetics of the Sea", AGARD-CP-77-70; November 1970. Based on this article, the optical absorption appears to be the limiting factor in the optimum performance of any underwater system. That is, the light absorbed by the water and particulate matter in the water is not merely redistributed but is transformed into heat and is lost as prospective information.

The absorption mean free path for the "blue-green" window ranges from a few tens of centimeters or less in dirty harbors to tens of meters in very clean ocean waters. At other wavelengths, the absorption mean free path is much shorter. Thus, even in clear ocean water, optimum system performance is limited to just a few hundred meters of operational range. For example, if a 1000-joule laser pulse is transmitted through 30 meter water and no scattering occurs, then only a single photon will be left after a range of 1.5 km. Increasing the signal power by an order of magnitude only extends the above range by 70 m. Coupling these pulses with normal imaging/communications requirements, e.g. having a minimum system signal-to-noise ratio in view of the inherent background noise sources in seawater, just further increases the signal energy requirements by several orders of magnitude, even in the clearest of ocean waters. Unfortunately, because of the foregoing constraints, electro-optical technology limitations generally force the proposed system's operational range to be reduced. Thus, an accurate determination of real-world volume absorption coefficients is mandatory for a true assessment of a system and its importance to this assessment cannot be overestimated.

The importance of being able to determine the true absorption coefficients becomes of greater significance when a practical application of optical communication or ranging is to be attempted in the field. At present, no in situ measurement techniques exist for determining the true absorption coefficient "a" of particulate media under field conditions. Several methods have been proposed as noted in the article identified above, but are generally limited to very homogenous and static paths. No known approach addresses itself to a method for determining the true absorption coefficient in situ of both homogenous and inhomogenous dynamic particulate scattering media, e. g. several different volumes of ocean water, over extended paths using pulsed laser techniques. This capability needs further manifestation to provide researchers and designers with necessary design parameters from which devices can be fabricated to enable more reliable undersea communications.

Thus, there exists a continuing need in the state-of-the-art for an in situ method for determining the absorption coefficient of pulsed light energy through a variety of long-path media which is capable of a nearly real-time analysis by moderately skilled technicians.

SUMMARY OF THE INVENTION

The present invention is directed to providing a method for determining in situ the true absorption coefficient of a particulate medium. First there is the pulsing of a beam of radiation through a relatively wide path in the particulate medium. A radiation detector located a distance away from the source of the pulsed beam receives the radiation at the end of the wide path and reproduces electronically signals created by both the absorption and particulate multiple scattering effects of the particulate medium. A monitoring of the representative signals includes a comparison thereof and a determination of which components are attributed to the absorption of the medium and the particulate scattering of the medium so as to arrive at an accurate representation of the medium's absorption coefficient.

It is a prime object of the invention to provide a method by which the total absorption coefficient is determined.

Yet another object is to provide a method for indicating the true absorption coefficient during an in situ analysis.

Still another object is to provide a method by which the absorption and particulate scattering components of the absorption coefficient are individually identified.

Still another object is to provide a method for determining the absorption coefficient of a given medium which is rigidly performed by a moderately skilled technician in an in situ analysis.

Still another object is to provide a highly reliable, uncomplicated method for performing an in situ analysis of the absorption coefficient of a given fluid medium to enable more reliable communications and ranging therethrough.

Still another object is to provide a method of determining an in situ absorption coefficient analysis which is performed at a reduced cost.

These and other objects of the invention will become more readily apparent from the ensuing description and claims when taken with the accompanying drawings.

DESCRIPTION OF THE PREFERRED EMBODIMENT

Figure 1C:
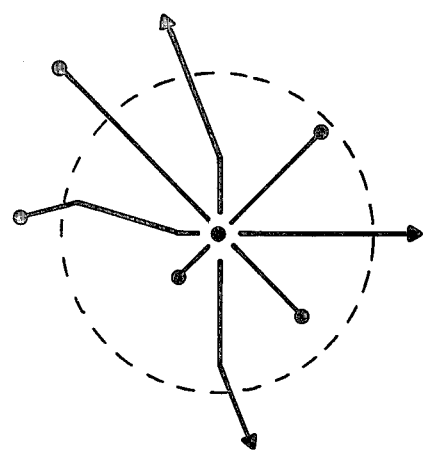
FIGS. 1a, 1b and 1c schematically depict the constituent parts indentifiable in an absorption coefficient analysis of a given fluid medium.
Figure 1B:
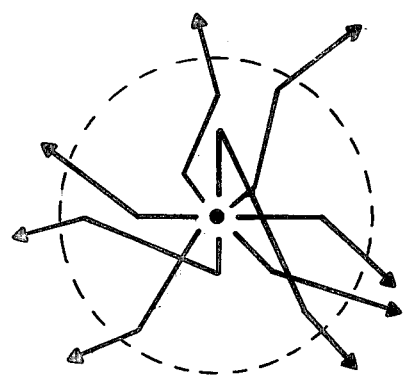
Figure 1A:
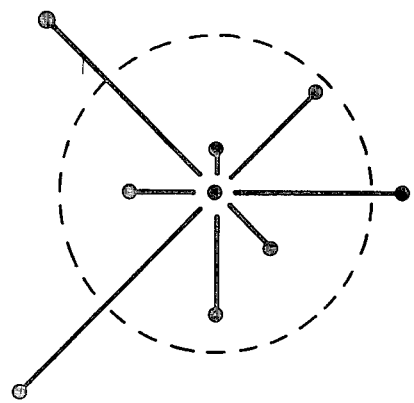

In principle, the electro-optical phenomenon sought to be measured by an absorption meter is shown in FIGS. 1a, 1b and 1c. For the purposes of analysis, a point source of light is said to be located at the center of a spherical irradiance detector of radius R. If the volume is filled between the detector shell and the light source with an absorbing, nonscattering medium, then the normalized power received is equal to $$P_o/P_I = \exp[-aR] \quad (1)$$

with
$P_o$ = received power
$P_I$ = initial total power of source
a = volume absorption coefficient
R = radius of shell Such is the case as shown in FIG. (1a). Now, however, if the volume within the shell is filled rather with a uniform nonabsorbing, totally scattering medium, then $$P_o/P_I = 1 \quad (2)$$

and the scattering of photons ideally can be portrayed as shown in FIG. (1b).

More realistically, and particularly in the case of a nonhomogeneous medium, if the shell's volume is filled with an absorbing, scattering medium, the situation shown in FIG. (1c) is created and $$P_o/P_I = \exp -aR(1+\delta) \quad (3)$$

with $\delta$ = excess average mean path correction due to particulate multiple scattering of the initial radiation distribution.

The quantity $\delta$ is generally considered small, e.g. a second order effect, and usually is ignored. For example, two more recently reported theoretical models for optical propagation through particulate scattering media neglect this facet. see D. Arnush, "Underwater light-beam propagation in the small-angle-scattering approximation" *J. O. S. A.*, 62, No. 9, pp1109–11 (1972) and L. B. Stotts, "The radiance produced by laser radiation traversing a particulate multiple-scattering medium", *J. O. S. A.*, 67, No 6, pp815–19 (1977). Both neglected $\delta$ because the validity range limitations of the analysis were incurred by the use of the small-angle-scattering approximation. Conventional field absorption meters are usually designed to minimize the effect of this parameter on the measured absorption coefficient. For example, by keeping the source/detector separation on the order of 0.5 m, the error in the measured value due to scattering is less than 1 percent for a likely value of the conventional scattering coefficient S which translates to $\leq 2.2$ dB/m and less than 10 percent even in waters with a scattering coefficient as large as 2 $m^{-1}$ or 8.7 dB/m. These values were arrived at and documented in the article by G. D. Gilbert entitled "Optical Absorption Meter" SRI project 7440 Contract N60530-68-C-1423 April '69.

Thus, the general impact of ignoring $\delta$ is to limit the absorption measurement process to short, optically thin and homogenous propagation paths. Contrary to the contemporary approaches, the measuring of the volume absorption coefficient proposed by this inventive concept does not ignore the effects of $\delta$ and, hence, is not limited to the propagation conditions set forth above. H. M. Heggestad in his report entitled "Optical Communications Through Multiple Scattering Media," MIT Tech. Report No 472, Nov. 22, 1968 and E. A. Bucher in "Computer Simulation of Light Pulse Propogation for Communications through Thick Clouds, "*Applied Optics* 12, No. 10, pp2391-2400 (1973) have both shown that the average excess mean path traversed by scattered photons is directly related to the multipath time spread incurred by a laser pulse in propagating through a particulate scattering medium. In fact, since the particulate multiple scattering process is exponentially distributed statistically, it is easy to show that $$\delta = 0.71 \left( \frac{C \Delta t}{R} \right) \quad (4)$$

where
C = Speed of light in ocean water and
$\Delta t$ = multipath time spread

Thus, for a spherical detector, we have $$\delta = \frac{-\ln(P_o/P_I)}{[R + 0.71 C \Delta t]} \quad (5)$$

Unfortunately, a spherical detection shell of a large radial dimension is impractical. However, if we use a flat, cosine detector in conjunction with pulsed laser transmitter, an effective absorption meter can be made which can be fielded and is not subject to the normal measurement limitations of conventional meters.

Figure 2:
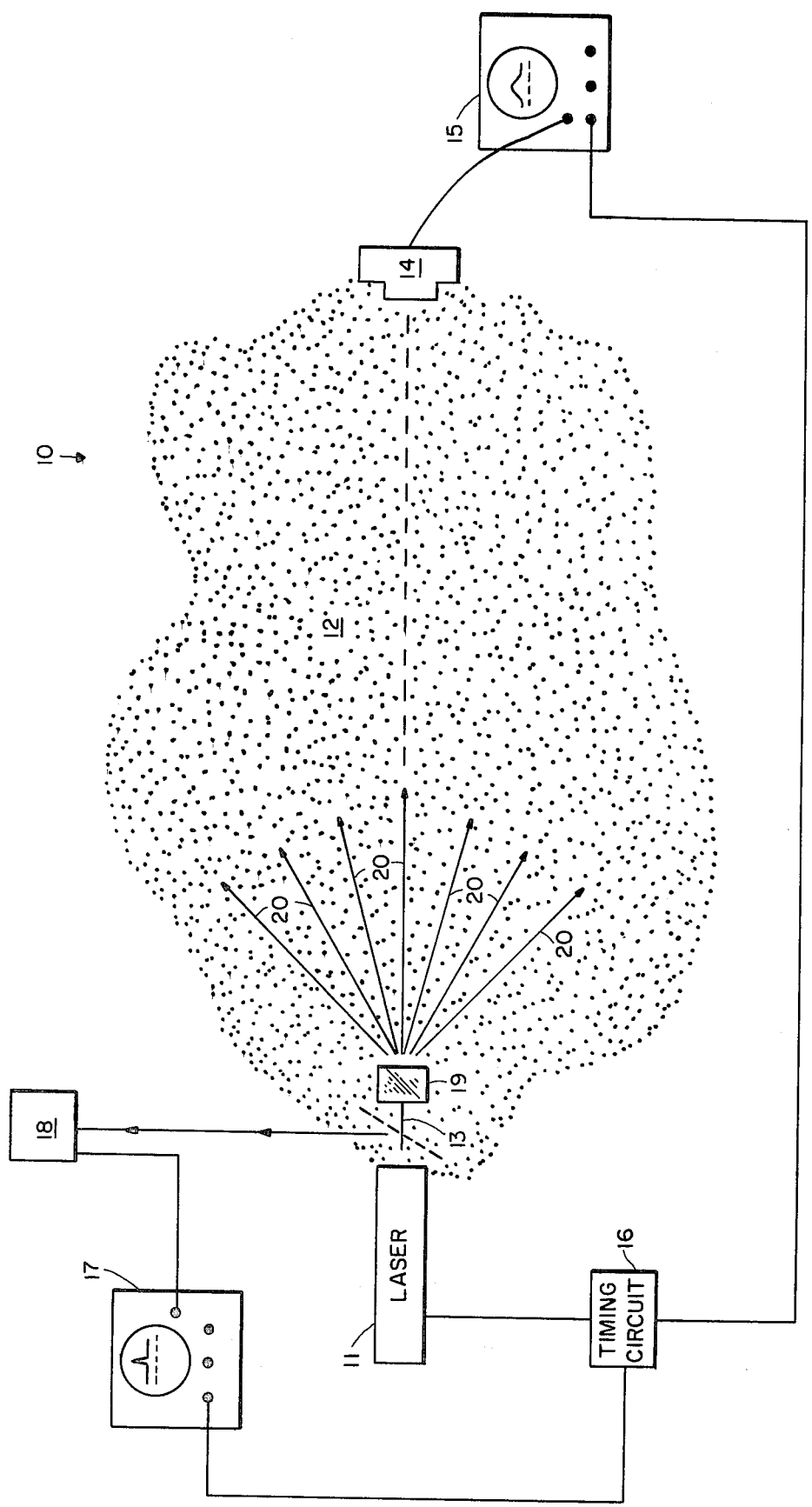
FIG. 2 is a schematic representation of the apparatus of the method of this invention.
Figure 3:
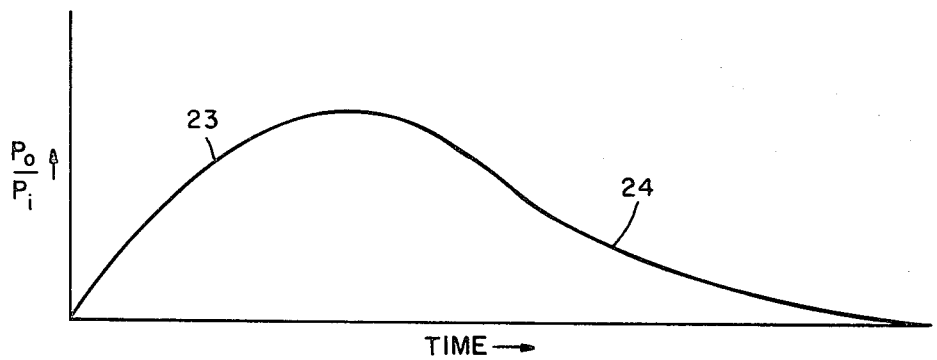
FIG. 3 depicts the waveforms of the constituent parts of the results of an in situ analysis.

FIG. 2 illustrates the geometry of an absorption coefficient (a) meter 10. A pulsed laser transmitter 11 is situated within an absorptive, particulate multiple scattering medium 12 and the orientation of its beam 13 such that its optic axis is colinear with the inverse normal of the surface comprising a flat, cosine detector 14. The laser transmitter and a monitoring and discriminating device 15, such as a high speed storage scope, are synchronized by a timing circuit 16 so that an irradiating pulse is displayed on a scope 17 and later at device 15. The signal transmitted by the laser is intercepted and fed to scope 17, for display via a detector 18 (as schematically shown).

The output of the laser is modified by an optical diffuser 19 to produce a radiance distribution 20 which is Lambertian in nature; for example, this could be accomplished by diverging the initial beam through an optical diffuser such as opal glass. Thus, for all practical purposes, the isotropic source scattering scenario referred to in FIGS. 1a, 1b, and 1c is recreated for the meter 10.

The normalized received power at the irradiance meter is equal to $$P_o/P_I = \frac{A_{rec}}{4\pi R^2} e^{-aR(1+\delta)} \quad (6)$$

where $A_{rec}$ = area of the irradiance meter.

Rewriting equation (6) in view of equation (4) gives an expression for the integrated absorption coefficient of the form $$a = \frac{-\ln(P_o/P_I) + \ln\left(\frac{A_{rec}}{4\pi R^2}\right)}{[R + 0.71 C \Delta t]} \quad (7)$$

Thus, by measuring ($P_o/P_I$) and t and knowing the area and R, one can obtain the absorption coefficient "a".

The constituents 23 and 24 of the signal received at the dectector and monitored and analyzed and are respectively gausian and exponential in shape. They represent the signal due to absorption and scattering respectively and when compared to known waveforms previously obtained from known fluids, the absorption coefficient of the unknown medium is determined.

Figure 4:
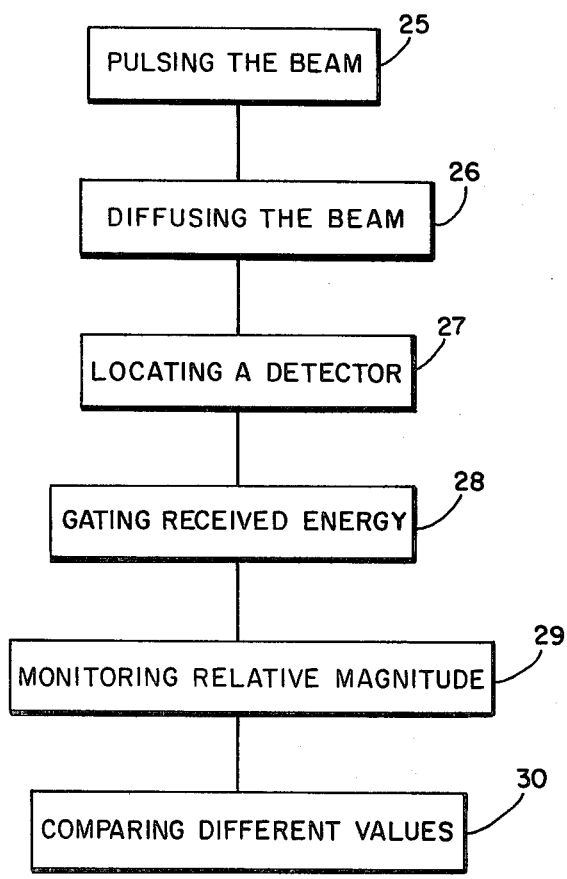
FIG. 4 represents the method of the invention for implementing a fluid analysis.

The novel method assuring the in situ measurement of the absorption coefficient is depicted in FIG. 4 and, first, calls for there being a pulsing 25 of a beam of optical radiation through a particular medium and optionally, diffusing 26 of the beam. Optionally, there is a maintaining of the pulsing of a beam a distance from the location of a detector to assure a monitoring of representative signals. Next, there is the locating 27 of a suitable detector and a gating of the received energy to enable a monitoring 29 of the relative magnitude to determine the absorption coefficient; the step of monitoring optionally includes the comparing 30 of the different values representative of the relative magnitudes with known values previously obtained from known fluids to allow a reliable determination of the absorption coefficients.

Obviously, many other modifications and variations of the present invention are possible in the light of the above teachings. It is therefore to be understood that within the scope of the appended claims the invention may be practiced otherwise than as specifically described.

What is claimed is:

1. A method for determining in situ the true absorption coefficient of a particulate media comprising:
    pulsing a beam of optical radiation through a wide path in the particulate medium;
    locating a radiation detector to receive the radiation at the end of the wide path;
    actuating the detector for predetermined intervals to pass signals each representative of both the absorption and particulate multiple scattering of the particulate media as the beam passes therethrough; and
    monitoring the magnitudes of the representative signals by comparing the representative signals to known values to determine the absorption coefficient.

2. A method for determining in situ the true absorption coefficient of a particulate media comprising:
    pulsing a beam of optical radiation through a wide path in the particulate medium, the step of pulsing includes the diffusing of the beam for radiation through the particulate media;
    locating a radiation detector to receive the radiation at the end of the wide path;
    actuating the detector for predetermined intervals to pass signals each representative of both the absorption and particulate multiple scattering of the particulate media as the beam passes therethrough; and
    monitoring the magnitudes of the representative signals by comparing the representative signals to known values to determine the absorption coefficient.

* * * * *